US008664614B2

(12) United States Patent
Agano et al.

(10) Patent No.: US 8,664,614 B2
(45) Date of Patent: Mar. 4, 2014

(54) RADIOGRAPHIC IMAGING METHOD, RADIATION DETECTOR AND RADIOGRAPHIC IMAGING APPARATUS

(71) Applicant: FUJIFILM Corporation, Tokyo (JP)

(72) Inventors: Toshitaka Agano, Ashigarakami-gun (JP); Yasuko Yahiro, Ashigarakami-gun (JP); Takao Kuwabara, Ashigarakami-gun (JP); Yasunori Ohta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/039,723

(22) Filed: Sep. 27, 2013

(65) Prior Publication Data

US 2014/0027650 A1    Jan. 30, 2014

Related U.S. Application Data

(63) Continuation of application No. PCT/JP2012/001921, filed on Mar. 21, 2012.

(30) Foreign Application Priority Data

Mar. 28, 2011 (JP) .................................. 2011-070402

(51) Int. Cl.
*G01T 1/24* (2006.01)
(52) U.S. Cl.
USPC ..................................................... 250/370.08

(58) Field of Classification Search
USPC ........ 250/361 R, 362, 363.01, 363.02, 370.01, 250/370.08, 370.09, 393
See application file for complete search history.

(56) References Cited

U.S. PATENT DOCUMENTS

2010/0208958 A1    8/2010   Yamada et al.

FOREIGN PATENT DOCUMENTS

| JP | 2005-7061 A | 1/2005 |
|---|---|---|
| JP | 2010-110571 A | 5/2010 |
| JP | 2010-187916 A | 9/2010 |

OTHER PUBLICATIONS

International Search Report Issued in PCT/JP2012/001921, mailed on Jul. 3, 2012.
PCT/ISA/237—Mailed on Jul. 3, 2012, issued in PCT/JP2012/001921.

*Primary Examiner* — Mark R Gaworecki
(74) *Attorney, Agent, or Firm* — Birch, Stewart, Kolasch & Birch, LLP

(57) ABSTRACT

A radiation detector for detecting irradiated radiation that includes: a converting layer for converting radiation irradiated from a radiation source capable of irradiating radiation from two imaging directions, which are different from each other, into electric charges; and a plurality of pixel electrodes for collecting the converted charges. In the radiation detector, when at least one of the two imaging directions forms a specified angle θ with respect to the direction that is orthogonal to the detector plane of the radiation detector, the thickness d of the converting layer and the sizes p of the pixel electrodes satisfy the condition: d·tan θ<k·p (k is a constant of 1 or less).

11 Claims, 5 Drawing Sheets

FIG.5
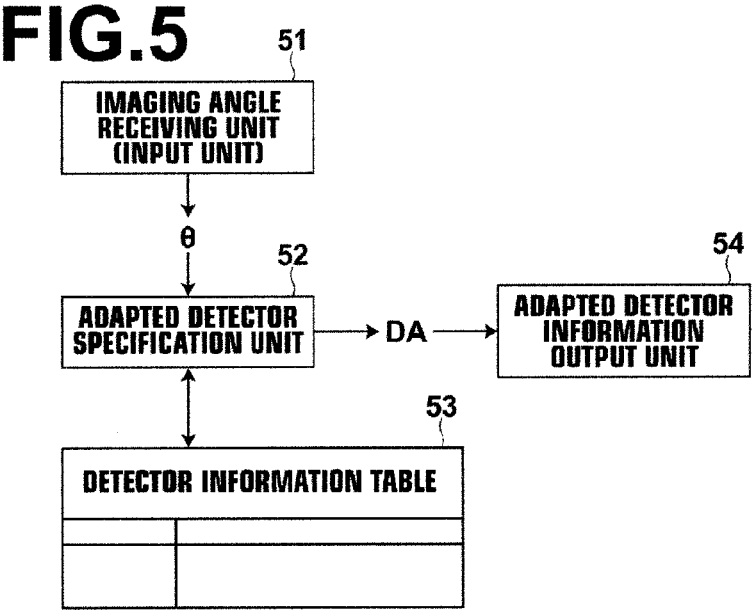
FIG.6
| DETECTOR IDENTIFICATION INFORMATION | MAXIMUM IMAGING ANGLE $\theta_{max}$ |
|---|---|
| RADIATION DETECTOR A | 14° |
| RADIATION DETECTOR B | 20° |
| RADIATION DETECTOR C | 8° |
FIG.7
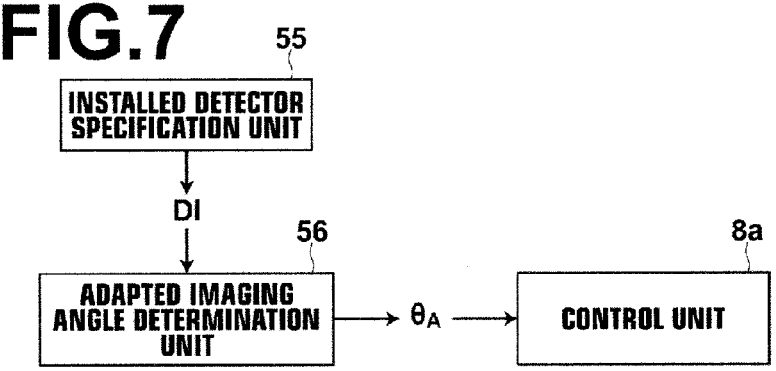

RADIOGRAPHIC IMAGING METHOD, RADIATION DETECTOR AND RADIOGRAPHIC IMAGING APPARATUS

CROSS REFERENCE TO RELATED APPLICATIONS

This application is a Continuation of PCT International Application No. PCT/JP2012/001921 filed on Mar. 21, 2012, which claims priority under 35 U.S.C 119(a) to application No. 2011-070402 filed Mar. 28, 2011 in Japan, all of which are hereby expressly incorporated by reference into the present application.

FIELD OF THE INVENTION

The present invention relates to a technique for generating radiographic images for the right and left eyes, so as to achieve stereoscopic viewing by using binocular parallax.

DESCRIPTION OF THE RELATED ART

Conventionally, enabling stereoscopic viewing utilizing parallax by combining a plurality of images for display thereof has been known. Such images which can be stereoscopically viewed (hereinafter referred to as stereoscopic images or stereo images) are generated based on a plurality of images having parallax thereamong, obtained by imaging the same subject from different positions.

Further, generating such stereoscopic images is utilized not only in the fields such as digital cameras and television, but also in the field of radiographic imaging. That is, radiation is irradiated from directions which are different from each other into a subject, and the radiation transmitted through the subject is detected by a radiographic imaging detector, respectively to obtain a plurality of photographic images having parallax thereamong so that the stereoscopic images are generated based on these radiographic images. Moreover, the stereoscopic images are generated in such a way, so that radiographic images having a sense of depth can be observed, and further, radiographic images which are more suitable for diagnosis can be observed (see, Patent Document 1 (Japanese Unexamined Patent Publication No. 2010-110571), for example).

SUMMARY OF THE INVENTION

In the radiographic imaging apparatus which obtains stereo images as described above, at least one of a plurality of imaging directions is set to form an angle of between about 4 and 15 degrees with respect to a direction that is orthogonal to a detector plane of a radiation detector. In this manner, in the case that radiation is irradiated from a direction that is slanted with respect to the radiation detector, electric charges generated at a point A in the vicinity of an upper surface of a converting layer 101 which converts radiation into electric charges are collected by a pixel electrode 102b, as schematically shown in FIG. 8. In contrast, electric charges generated at a point B in the vicinity of a lower surface of the converting layer 101 are likely to be collected by the pixel electrode 102a which is adjacent to the pixel electrode 102b, according to imaging angles, instead of being collected by the pixel electrode 102b. In this case, radiographic image information about a specific location of a subject, which is obtained through transmission and absorption of radiation within the subject, is recorded across a plurality of pixels, and thereby blurring occurs in the generated radiographic images.

The present invention has been developed in view of the foregoing circumstances. It is an object of the present invention to provide a radiographic imaging method, a radiation detector, and a radiographic imaging apparatus that reduce blurring of radiographic images that arises from radiation irradiated from a direction that is slanted with respect to the radiation detector being detected across a plurality of pixels in the radiation detector.

A radiographic imaging method according to the present invention comprises the steps of:

irradiating radiation from a predetermined first imaging direction;

detecting the radiation irradiated from the first imaging direction by a radiation detector having a converting layer for converting the radiation into electric charges and a plurality of pixel electrodes for collecting the converted electric charges;

irradiating radiation from a second imaging direction which is different from the first imaging direction;

detecting the radiation irradiated from the second imaging direction by the radiation detector; and controlling at least one of the first and the second imaging directions to form a predetermined angle with respect to a direction that is orthogonal to a detector plane of a radiation detector; wherein a thickness d of the converting layer, a pixel size p and the predetermined angle θ satisfy the following formula (1).

$$d \cdot \tan \theta < k \cdot p \qquad (1)$$

The radiation detector according to the present invention has a converting layer for converting radiation irradiated from a radiation source which is capable of irradiating radiation from two imaging directions, which are different from each other, into electric charges and a plurality of pixel electrodes for collecting the converted electric charges detects the irradiated radiation, wherein in the case that at least one of two imaging directions forms a predetermined angle with respect to a direction that is orthogonal to a detector plane, a thickness d of the converting layer, a pixel size p and the predetermined angle θ satisfy the following formula (1).

$$d \cdot \tan \theta < k \cdot p \qquad (1)$$

In this case, k is a constant of 1 or less, and preferably 0.5 or less.

The radiographic imaging apparatus according to the present invention includes a radiation source capable of irradiating radiation from two imaging directions, which are different from each other, and the above radiation detector.

Further, the above radiographic imaging apparatus may further be provided with a mechanism which can be selectively equipped with a plurality of the radiation detectors having a different thickness d of the converting layer and/or a different size p of the pixels, individually; an imaging angle setting means for receiving a setting of the predetermined angle θ; and an adapted detector specification means for specifying the radiation detector that satisfies formula (1) at the set predetermined angle θ.

Further, the above radiographic imaging apparatus may further be provided with a mechanism which can be selectively equipped with a plurality of the radiation detectors having a different thickness d of the converting layer and/or a different size p of the pixel, individually; a detector specification means for specifying a radiation detector which has been equipped therewith; and an adapted imaging angle determination means for determining a predetermined angle θ that satisfies formula (1) in the identified radiation detector.

According to the present invention, when radiation irradiated from two imaging directions, which are different from each other, at least one of two imaging directions forms a predetermined angle θ with respect to a direction that is orthogonal to a detector plane of a radiation detector and a thickness d of the converting layer and a pixel size p of the radiation detector satisfy the following formula (1) (k is a constant of 1 or less).

$$d \cdot \tan \theta < k \cdot p \tag{1}$$

Thereby, in a typical example as schematically shown in FIG. 1, the electric charges generated at a point A in the vicinity of an upper surface of the radiation detector 101 as well as the electric charges generated at a point B in the vicinity of a lower surface by the radiation irradiated from a direction that is slanted with respect to the radiation detector are collected by the same pixel electrode 102b. Therefore, blurring of radiographic images that is caused by radiation irradiated from a direction which is slanted with respect to the radiation detector being detected across a plurality of pixels in the radiation detector will be reduced, and the quality of stereoscopic display of radiographic images will be improved as well.

BRIEF DESCRIPTION OF THE DRAWINGS

FIG. 5 is a block diagram representing a configuration unique to a second embodiment of the present invention;

FIG. 6 is a diagram representing one example of a detector information table;

FIG. 7 is a block diagram representing a configuration unique to a third embodiment of the present invention.

DESCRIPTION OF THE PREFERRED EMBODIMENTS

Hereinafter, the stereo mammography display system according to embodiments of the present invention will be described with reference to the drawings. At first, schematic configurations and actions of the mammography display system according to a first through third embodiments of the invention will be described, and then the characteristic portions of each embodiment of the invention will be described.

Figure 2:
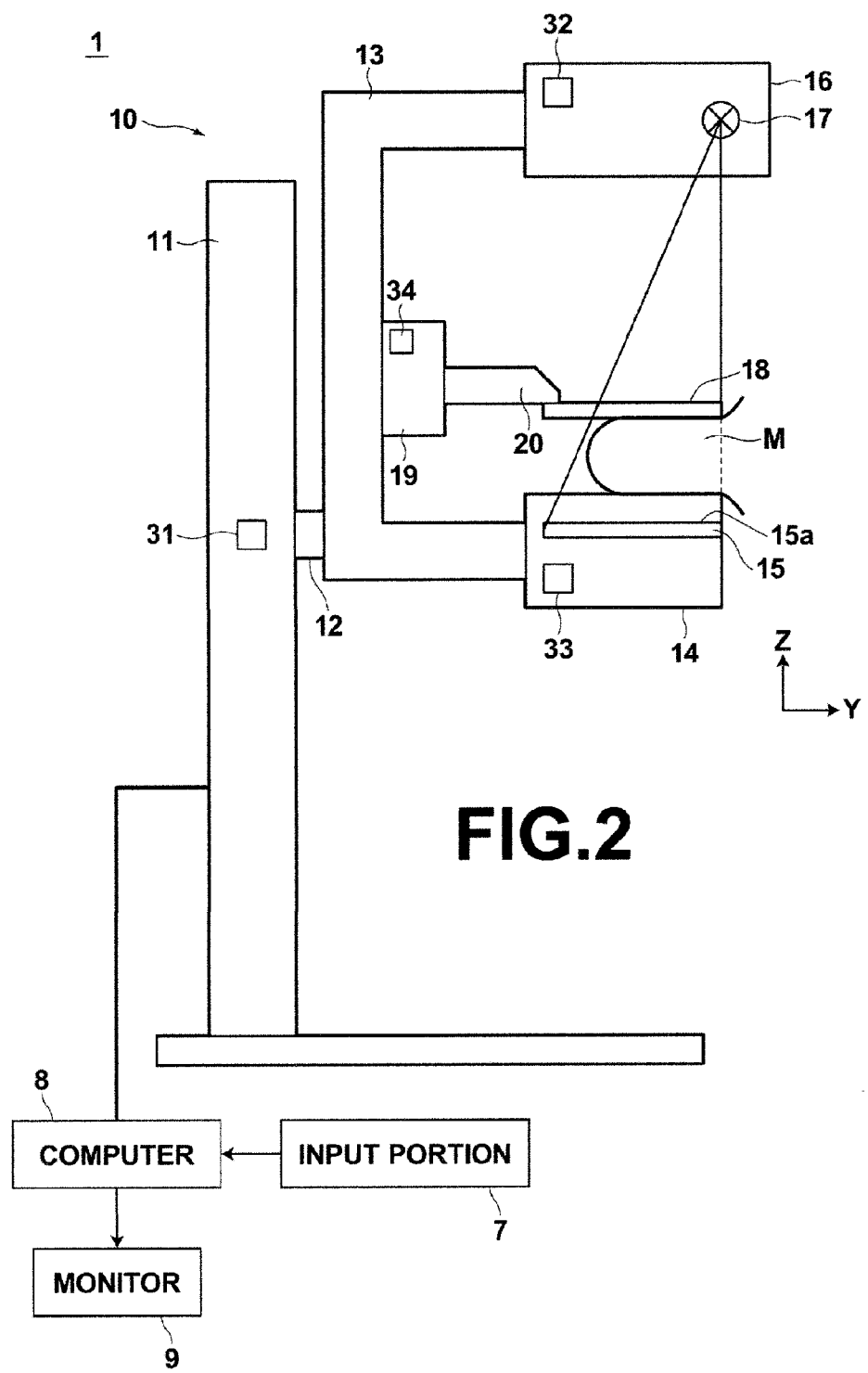
FIG. 2 is a schematic configuration diagram of a stereo mammography display system according to an embodiment of the present invention.
Figure 3:
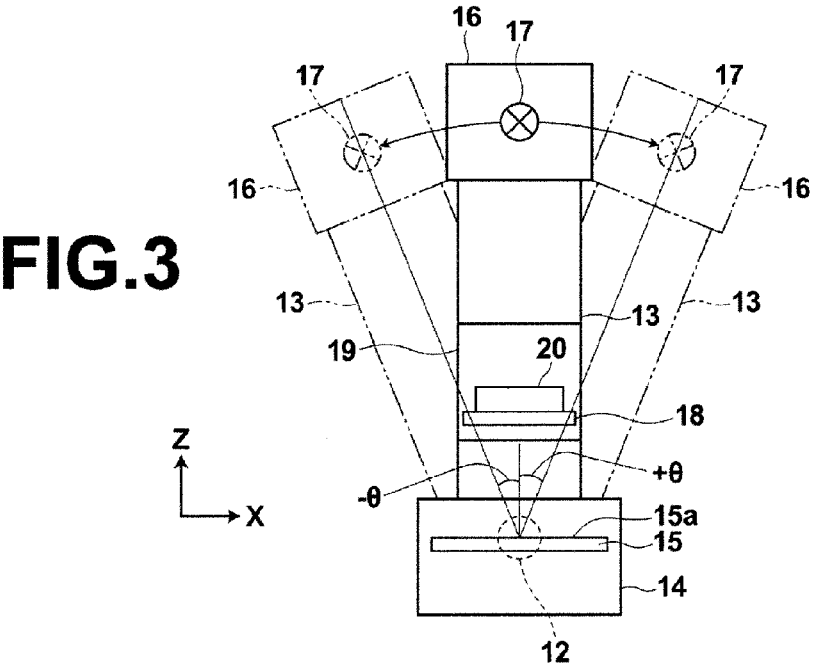
FIG. 3 is a view from the right side of an arm part of the stereo mammography display system of FIG. 2.
Figure 4:
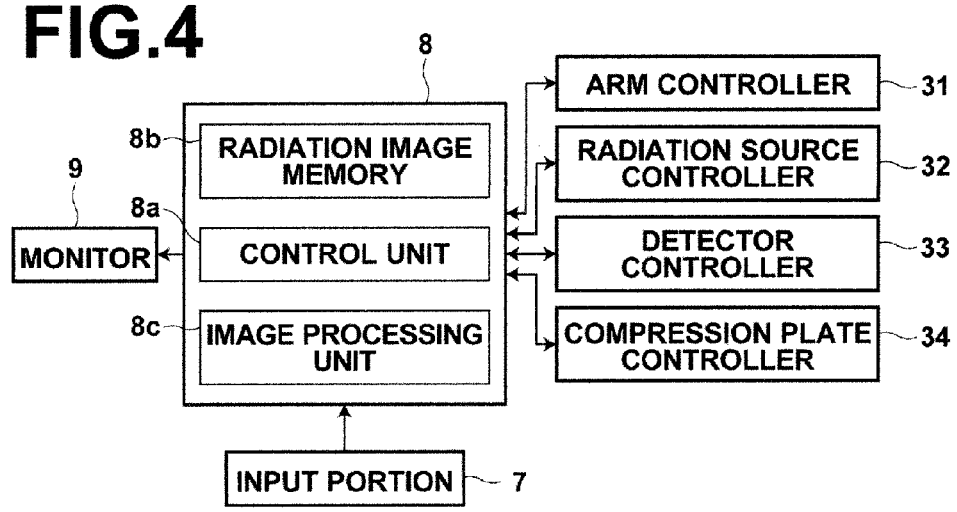
FIG. 4 is a block diagram illustrating the schematic configuration within a computer of the stereo mammography display system shown in FIG. 2.
Figure 8:
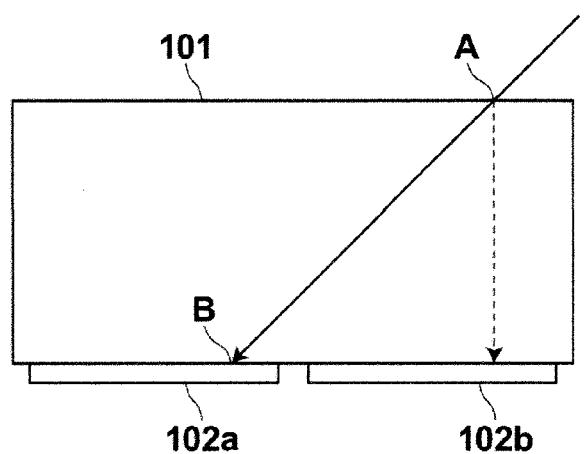
FIG. 8 is a diagram schematically illustrating a relationship among a thickness of a converting layer and a pixel size and an incident angle of radiation in a conventional radiation detector.

FIG. 2 is a schematic configuration diagram of a stereo mammography display system, FIG. 3 is a view from the right side of an arm part of the stereo mammography display system of FIG. 2; and FIG. 4 is a block diagram illustrating the schematic configuration within a computer of the stereo mammography display system shown in FIG. 2.

The mammography display system 1 of this embodiment includes a mammography device 10, a computer 8 connected to the mammography device 10, a monitor 9 connected to the computer 8 and an input portion 7, as shown in FIG. 2.

Further, the mammography device 10 includes a base 11, a rotatable shaft 12 which is rotatable and is capable of moving vertically (in a Z direction) along the base 11, and an arm part 13 coupled to the base 11 via the rotatable shaft 12. Please note that FIG. 3 shows the arm part 13 which is viewed from the right direction of FIG. 2.

The arm part 13 is in the shape of the letter C. The arm part 13 is provided with a imaging platform 14 at one end thereof, and a radiation irradiation unit 16 that faces the imaging platform 14 at the other end thereof. The rotation and the vertical movement of the arm part 13 are controlled by an arm controller 31 incorporated in the base 11.

The imaging platform 14 includes a radiation image detector 15 such as a flat panel detector, and a detector controller 33 which controls reading out charge signals from the radiation image detector 15 therein. Further, the imaging platform 14 also includes a circuit board in which a charge amp that converts the charge signals read out from the radiation image detector 15 into voltage signals, a correlation double sampling circuit that samples the voltage signals output from the charge amp, and an AD converter that converts the voltage signals into digital signals are provided.

Further, the imaging platform 14 is designed to be rotatable with respect to the arm part 13 so that even when the arm part 13 rotates with respect to the base 11, the imaging platform 14 can be oriented in a direction that is fixed with respect to the base 11.

The radiation image detector 15, which has a converting layer that converts radiation into electric charges and a plurality of pixel electrodes that collect the converted electric charges, can repeatedly record and read radiation images. Radiation image detectors which are directly exposed to radiation to generate electric charges, i.e., direct conversion type radiation image detectors, or radiation image detectors that convert radiation into visible light at first and then convert the visible lights into charge signals, i.e., indirect conversion type radiation image detectors, may be employed. Further, it is preferable for the radiation image signal readout system to be a TFT read-out system that turns TFT (thin film transistor) switches ON/OFF to read out radiation image signals, or an optical readout system that irradiates reading light to read out radiation image signals. However, the readout system is not limited to those listed above, and other systems may be employed. A/D conversion is performed on the radiation image signals output from the ration image detector 15 to generate radiation image data. Note that the features unique to the embodiments of the present invention will be described later.

The radiation irradiation unit 16 houses a radiation source 17 and a radiation source controller 32 therein. The radiation source controller 32 is designed to control the irradiating timing of radiation from the radiation source 17 and the radiation generation conditions (tube voltage, tube current, time, tube current-time product and the like) of the radiation source 17.

Further, the arm part 13 is provided with a compression plate 18 located above the imaging platform 14 for holding down and compressing a breast M at the center thereof, a support part 20 for supporting the compression plate 18 and a movement mechanism 19 for moving the support part 20 vertically (in the Z direction). A compression plate controller 34 controls the position and compression pressure of the compression plate 18.

The computer 8 includes a Central Processing Unit (CPU) and a storage device such as a semiconductor memory, hard disk, SSD, or the like, and these hardware components constitute a control unit 8a, a radiation image memory 8b and an image processing unit 8c, as shown in FIG. 4.

The control unit 8a is designed to output predetermined control signals toward various types of controllers 31 through 34 to control the whole system. The specific control method will be described later. The radiation image memory 8b is designed to store radiation image data for each imaging angle obtained by the radiation image detector 15. The image processing unit 8c is designed to perform various image processes on the radiation image data.

The input portion 7 is constituted by pointing devices such as a keyboard, a mouse and the like, and is designed to receive inputs of imaging conditions and operation instructions by a photographer.

The monitor 9 is designed to display the radiation images for each photographing direction as two-dimensional images, individually by using two radiation image data output from the computer 8 so as to display stereo images.

The configuration that displays stereo images may be a configuration, for example, in which radiation images are individually displayed based on two sets of radiation image data using two screens, and one of the radiation images is projected to the right eye of an observer and the other radiation image is projected to the left eye of the observer using a half mirror or polarization glasses so as to display stereo images.

Alternatively, for example, a configuration, in which two radiation images are shifted only by a predetermined amount of parallax to be overlapped with each other so that stereo images can be generated by observing this with the polarization glasses, may be employed. As a further alternative, a configuration, in which two radiation images are displayed by a 3D liquid crystal display that enables stereoscopic viewing to generate stereo images as in the parallax barrier system and the lenticular system may also be employed.

Further, the apparatus that displays stereo images and the apparatus that displays two-dimensional images may be configured separately, but may be configured as a single apparatus in the case that the images can be displayed on the same screen.

Next, the actions common to the mammography display system of each embodiment will be described.

The breast M is placed on the imaging platform 14 at first, and then the breast M is compressed under a predetermined pressure by the compression plate 18.

Next, imaging conditions are input by the input portion 7. In the present embodiment, detailed imaging conditions such as an imaging angle, the amount of radiation and the like are stored for each imaging mode in the memory within the computer 8. When an imaging mode is selected in the input portion 7, the imaging conditions corresponding to the selected imaging mode are read out from the memory. In the present embodiment, the imaging modes include a normal mode and a stereo imaging mode. A case that the stereo imaging mode is selected will be described below. In the stereo imaging mode, imaging is performed twice at different angles $\theta$ so that two sets of radiation image data having angles (hereinafter referred to as angle of convergence $\theta$) formed by different imaging directions can be obtained. After the imaging mode is input, an instruction to start imaging will be input at the input portion 7.

When the instruction to start imaging is input at the input portion 7, stereo images of the breast M are imaged. In particular, the control unit 8a outputs information of the imaging angle $\theta$ that constitutes the angle of convergence 8 to the arm controller 31 at first. Please note that in the present embodiment, the combination of $\theta=0°$ and $\theta=4°$ is previously stored as the combination of the imaging angles $\theta$ to combine images for two-dimensional observation with images for stereoscopic display so as to reduce the number of imaging operations. Thereby, two sets of radiation image data having an angle of convergence $\theta'=4°$ can be obtained. Radiation image data obtained at imaging angle $\theta=0°$ are used for both two-dimensional observation and stereoscopic display.

The arm controller 31 receives information of the imaging angle $\theta$ output from the control unit 8a and outputs control signals which cause the arm unit 13 to be slanted in a direction that is vertical to the detector plane 15a by 4° as the imaging angle $\theta$, based on the information of the imaging angle $\theta$.

The arm unit 13 rotates by 4° in response to the control signals output from the arm controller 31. Then, the control unit 8a outputs control signals which causes the radiation source controller 32 to irradiate an amount of radiation according to the imaging conditions and outputs control signals which causes the detector controller 33 to read out radiation images as well. In response to the control signals, the radiation source 17 irradiates the amount of radiation according to the imaging conditions, and the radiation image detector 15 detects a radiation image of the breast M which has been imaged from a direction in which the imaging angle is 4° and the detector controller 33 reads out the radiation image data. Then, after the image processing unit 8c carries out a predetermined process, the radiation image memory unit 8b stores the processed radiation image data therein.

Then, the arm controller 31 outputs control signals which cause the arm unit 13 to be in a direction perpendicular to the imaging platform 14. That is, in the present embodiment, the control signals are output such that the imaging angle $\theta$, in which the arm unit 13 is vertical with respect to the detector plane 15, becomes 0°.

The arm unit 13 is caused to be in a direction perpendicular to the detector plane 15a in response to the control signals output from the arm controller 31. Then, the control unit 8a outputs control signals which causes the radiation source controller 32 to irradiate an amount of radiation according to the imaging conditions and outputs control signals which causes a detector controller 33 to read out radiation images as well. In response to the control signals, the radiation source 17 irradiates the amount of radiation according to the imaging conditions, and the radiation image detector 15 detects the radiation images of the breast M which has been imaged from a direction in which the imaging angle $\theta$ is 0°. After the imaging is completed, the compression plate 18 is moved to release the compression of the breast M, and the detector controller 33 reads out the radiation image data. After the image processing unit 8c carries out a predetermined process, the radiation image memory unit 8b stores the processed radiation image data therein.

Further, when stereo image display is requested by the user, the two sets of radiation image data stored in the radiation image memory 8b of the computer 8 are read out from the radiation image memory 8b and are subjected to a predetermined process to be output onto the monitor 9 so that the stereo images of the breast M are displayed on the monitor.

Moreover, when two-dimensional display is requested by the user, the set of radiation image data obtained at the imaging angle $\theta$ of 0° between the two sets of radiation images data stored in the radiation image memory 8b of the computer 8 is read out, and then a predetermined signal process is conducted thereon to be output onto the monitor 9 so that two-dimensional images of the breast M are displayed on the monitor 9.

The imaging operation and the image display operation are performed in the stereo imaging mode as described above.

Figure 1:
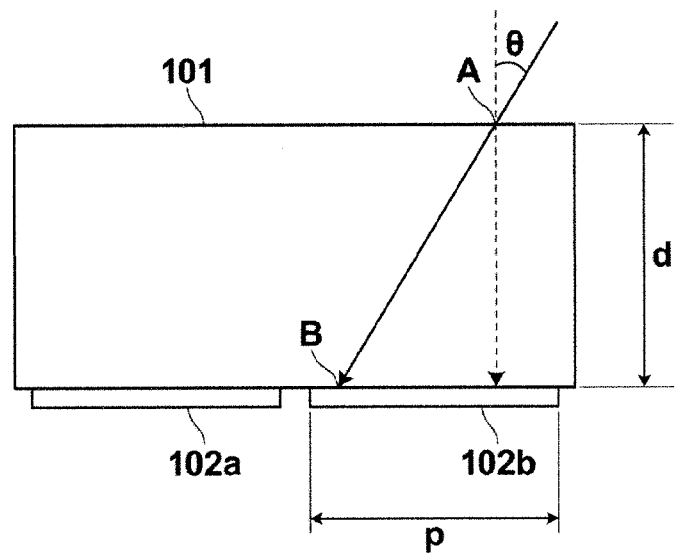
FIG. 1 is a diagram schematically illustrating a relationship among a thickness of a converting layer and a pixel size and an incident angle of radiation in a radiation detector according to the present invention.

In the first embodiment of the present invention, as schematically shown in FIG. 1, in the stereo imaging mode, the radiation image detector is used such that the thickness d of the converting layer 101, the size p of pixel electrodes 102a, 102b of the radiation image detector 15 and the imaging angle θ satisfy the following formula (1). The imaging angle θ is set in advance.

$$d \cdot \tan \theta < k \cdot p \quad (1)$$

In this case, it is preferable for k to be a constant of 1 or less and more preferably 0.5 or less.

In this manner, in the first embodiment according to the present invention, the difference between a position on the pixel electrodes where the electric charges generated in the vicinity of an upper surface of the converting layer 101 are collected and a position on the pixel electrodes where the electric charges generated in the vicinity of a lower surface of the converting layer 101 are collected is reduced to be less than a size of one pixel electrode (in the case that k=1) or less than half the size of the pixel electrode (in the case that k=0.5), such that blurring of radiation images, which arises from the radiation irradiated from a direction that is slanted with respect to the radiation image detector 15 being detected across a plurality of pixel electrodes 102a, 102b within the radiation detector 101, will be reduced and the quality of stereoscopic display of the radiation images will be improved.

In particular, if the angle of convergence θ' is too small or too large, appropriate stereoscopic viewing becomes difficult, and therefore it is desirable for the angle of convergence θ' to be set between 4° and 15°. Regarding two-dimensional observation, images taken from the front of the radiation image detector 15 are most appropriate therefor, and therefore it is desirable for the imaging angle θ for imaging images used for both the two-dimensional observation and the stereoscopic display to be 0. Accordingly, it is desirable for the imaging angle θ for radiation images used only for the stereoscopic display to be set between 4° and 15°. Therefore, in the stereo imaging mode according to the present embodiment, for example, the imaging angle can be set between 4° and 15° in advance according to the thickness d of the converting layer and the size p of pixel electrodes of the radiation image detector 15 used for imaging such that the above formula (1) is satisfied. Alternatively, the radiation image detector 15 having a thickness d of the converting layer and a size p of pixel electrodes that satisfy the above formula (1) at a predetermined imaging angle (e.g., 4°) may be designed/manufactured to be employed or may be selected from among existing products to be used. In this manner, the mammography display system 1 according to the present embodiment is designed such that the imaging angle θ, a thickness d of the converting layer and a size p of pixel electrodes of the radiation image detector 15 are optimized to satisfy the above formula (1) in the stereo imaging mode.

In the case that the radiation detector is of a direct conversion type TFT read-out system, for example, the detector comprises a semiconductor layer mainly containing amorphous selenium and the like and an upper bias electrode, which are laminated on an active matrix substrate on which TFT switches, a charge storage capacity and charge collection electrodes are two-dimensionally arranged. In the detector, the radiation transmitted through the subject is converted into electric charges in the semiconductor layer, and the electric charges are moved to the charge collection electrodes by voltage applied to the bias electrode. In this case, the semiconductor layer corresponds to the above converting layer 101, and the individual charge collection electrodes correspond to the above pixel electrodes 102a, 102b.

Further, in the case that the radiation detector is of a direct conversion type optical read-out system, for example, the detector comprises a first electrode layer that transmits recording electromagnetic waves carrying image information obtained by radiation transmitted through the subject at first; a recording photoconductive layer mainly containing amorphous selenium, which is exposed to the recording electromagnetic waves transmitted through the first electrode layer to generate charge pairs and exhibit a conductivity characteristic; a charge transport layer which functions as an insulator with respect to charges (stored charges) stored when recording the image information among the charges generated in the recording photoconductive layer and which functions as a conductor with respect to the stored charges and reverse-polarity transport charges; a reading photoconductive layer which is exposed to reading lights to generate charges; a second electrode layer including a plurality of a linear electrodes and a plurality of a second linear electrodes which are detecting electrodes for detecting signals corresponding to the charges generated in the recording photoconductive layer; and a transparent insulating layer which has insulation properties and that transmits the reading light; and a support that transmits the reading light. In this case, the recording photoconductive layer corresponds to the above converting layer 101. Moreover, the linear electrodes correspond to the pixel electrodes 102a, 102b, respectively, and the length in a short-side direction of each linear electrode corresponds to the size of pixel electrodes.

Further, in the case that the radiation detector is of an indirect conversion type TFT read-out system, for example, the detector comprises scintillator layers laminated on a circuit substrate. The scintillator layers are constituted by GOS ($Gd_2O_2S$) and convert the radiation transmitted through the subject into light. The circuit substrate includes photodiodes which receive the light generated in the scintillator layers to convert the light into charges and the TFT switches that read out the converted charges, which are two-dimensionally arranged on the circuit substrate. In this case, the scintillator layers correspond to the above converting layer 101. Further, the individual photodiodes correspond to the above pixel electrodes 102a, 102b, and the arrangement interval between the photodiodes corresponds to the size of pixel electrodes.

In the case of mammography having breasts as subjects, high-definition images are required, so that the pixel size should preferably be small. When this matter is considered, in the case that the imaging angle θ is set to 2° through 4°, the radiation image detector 15 that satisfies the above formula (1) can be a detector provided with a converting layer having a thickness of 150 μm through 300 μm and a size of pixel electrodes of 50 μm through 100 μm.

In the second embodiment according to the present invention, a detachably replaceable electronic cassette type of radiation image detector is employed as the radiation image detector 15. Further, the imaging angle θ can be arbitrarily set by the user, and a radiation image detector adapted to the set imaging angle θ is identified.

FIG. 5 is a block diagram representing a configuration unique to the second embodiment of the present invention. As shown in the figure, the computer 8 further includes an imaging angle receiving unit 51, an adapted detector specification unit 52, a detector information table 53 and an adapted detector information output unit 54.

The imaging angle receiving unit 51 is designed to receive input of an imaging angle θ using the input portion 7.

The adapted detector specification unit 52 refers to the detector information table 53 and specifies a radiation image detector 15 that is adapted to the input imaging angle θ.

FIG. 6 is a diagram representing one example of the detector information table 53. As shown in the figure, in the detector information table 53, the detector identification information for identifying radiation image detectors 15 is stored associated with the maximum value of the imaging angle (maximum imaging angle) $θ_{max}$ in the case of using the radiation image detectors 15 thereof. For example, a radiation detector A is registered such that the maximum imaging angle $θ_{max}$ is 14°. This maximum imaging angle $θ_{max}$ is a value that has been previously calculated by substituting a thickness d and a size p of pixel electrodes of the converting layer of each radiation image detector 15 into the above-mentioned formula (1).

The adapted detector specification unit 52 specifies a radiation image detector, in which the imaging angle θ received by the imaging angle receiving unit 51 is smaller than the maximum imaging angle $θ_{max}$ and the difference between the imaging angle θ and the maximum imaging angle $θ_{max}$ becomes smallest, from among a plurality of radiation image detectors registered in the detector information table 53, and outputs the identification information DA. In this case, the latter condition is based on the premise that the radiation image detector which has a smaller pixel size (the maximum imaging angle $θ_{max}$ is small) is favorable for mammography. Alternatively, the pixel size of each radiation image detector may also be set to be stored by being associated with radiation image detectors in the detector information table 53, so as to specify a radiation image detector having the smallest pixel size among the radiation image detectors that satisfy the former condition.

The adapted detector information output unit 54 outputs the information of the radiation detector that is adapted for imaging at the imaging angle θ onto the monitor 9. In particular, display of a message indicating "please install radiation image detector B" is performed. Alternatively, such message may indicate "the radiation image detector that is adapted to the input imaging angle has a thickness of the converting layer of between 150 and 300 μm and a pixel size of between 50 and 100 μm".

Thereby, the user can easily conceive of an appropriate radiation image detector to be installed with respect to a desired imaging angle θ.

Further, as a modified example of the present embodiment, the detector information table 53 may register detector identification information, a thickness d and a size p of pixel electrodes d of the converting layer of the radiation image detector with one another therein, and the adapted detector specification unit 52 may specify a radiation detector DA that is adapted to the input imaging angle θ by judging whether the above formula (1) is satisfied based on the registered thickness d of the converting layer, size p of pixel electrodes of each radiation image detector and the input imaging angle θ. Alternatively, the detector identification information may be registered by being associated with parameter values obtained by modifying the formula (1), e.g., k·p/d.

In the third embodiment of the present invention, a detachably replaceable electronic cassette type of radiation image detector is employed as the radiation image detector 15 in a manner similar to that of the second embodiment. Further, an appropriate imaging angle θ is set corresponding to the installed radiation image detector.

FIG. 7 is a block diagram representing a configuration unique to the third embodiment of the present invention. As shown in the figure, the computer 8 further includes an installed detector specification unit 55 and an adapted imaging angle determination unit 56.

The installed detector specification unit 55 obtains information (detector specification information DI) of a thickness d of the converting layer and a size p of pixel electrodes of the installed radiation image detector 15. In particular, a bar code representing the detector specification information DI may be attached to the radiation image detector 15, and the attached detector specification information DI is read out to be obtained. Alternatively, an IC chip, in which the detector specification information DI is stored, may be attached to the radiation image detector 15 to be read out. More specifically, readout methods may include a method that wirelessly receive the detector specification information stored in the IC chip in the same manner as a RFID tag. Further, the user can input the detector specification information DI from the input portion V.

The adapted imaging angle determination unit 56 calculates a maximum value of the imaging angle (maximum imaging angle) $θ_{max}$ in the case of using the installed radiation image detector 15 by substituting the thickness d of the converting layer and the size p of pixel electrodes into the above-described formula (1). Further, the imaging angle (adapted imaging angle) θA adapted for stereoscopic viewing is determined within a range smaller than the maximum imaging angle $θ_{max}$. For example, in the case that an imaging angle θB is previously found to be most appropriate for stereoscopic viewing, a determination is made such that θA=θB in the case that $θ_{max}$≥θB and θA=$θ_{max}$ in the case that $θ_{max}$<θB.

The control unit 8a reads the adapted imaging angle θA which has been determined by the adapted imaging angle determination unit 56 to be output to the aria controller 31.

Thereby, the imaging angle θA which is adapted for the installed radiation image detector 15 is automatically determined and imaging is performed at the determined imaging angle, so that the user does not need to manually adjust imaging angles.

Further, as a modified example of the present embodiment, a reference table, which stores the adapted imaging angle θA by associating it with each of the detector identification information, may be prepared in advance. In particular, a maximum imaging angle $θ_{max}$ can be calculated for each of the detector identification information based on the above-mentioned formula (1) and may be compared to an optimal imaging angle θB so that an adapted imaging angle θA can be specified and registered by being associated with the detector identification information in the table. In this case, the installed detector specification unit 55 specifies the detector identification information instead of a thickness d of the converting layer and a size p of pixel electrodes. Then, the adapted imaging angle determination unit 56 accesses the above reference table based on the detector identification information and obtains the adapted imaging angle θA associated with the detector identification information thereof.

The above embodiments are merely examples, and all of the above descriptions should not be applied to limit the technical scope of the present invention. Moreover, a system configuration, a hardware construction, a process flow, a module configuration, a user interface, specific processing details and the like, on which various alterations have been made without deviating from the spirit of the present invention in the above embodiments, are included in the technical scope of the present invention.

For example, the radiographic imaging apparatus of the present invention has been described as a mammography apparatus, but the subject is not limited to breasts. For example, the present invention may be applied to radiographic imaging apparatuses for imaging the chest, the head and the like.

Further, in each of the above embodiments, the imaging angle θ may be designed to be capable of being manually adjusted, and in the case that the adjusted imaging angle θ exceeds a maximum imaging angle $\theta_{max}$ calculated in advance by substituting a thickness d of the converting layer and a size p of pixel electrodes of the radiation detector into formula (1), a warning may be issued. Alternatively, in the first embodiment, the radiation image detector 15 may be designed to be detachable and to be provided with a processing unit for calculating a maximum imaging angle $\theta_{max}$ by substituting a thickness d and a size p of pixel electrodes of the converting layer of the installed radiation image detector into the above-mentioned formula (1), and in the case that the manually adjusted imaging angle θ exceeds the calculated maximum imaging angle $\theta_{max}$, a warning may be issued.

Alternatively, instead of using detachable radiation image detectors, a detector using a liquid scintillator may be employed and the amount of the liquid scintillator, i.e., the thickness of the converting layer, may be designed to be adjusted according to an imaging angle such that the above-mentioned formula (1) is satisfied.

Note that in each of the above embodiments, the number of imaging directions of radiation may be 3 or greater. In this case, at least one of the imaging directions, in which the above predetermined angle θ is different from 0°, merely needs to satisfy the above-mentioned formula (1). Further, it is preferable for all of the imaging directions, in which the above predetermined angle θ is different from 0°, to satisfy the above-mentioned formula (1).

What is claimed is:

1. A radiographic imaging method, comprising the steps of:
    irradiating radiation from a predetermined first imaging direction;
    detecting the radiation irradiated from the first imaging direction by a radiation detector having a converting layer for converting the radiation into electric charges and a plurality of pixel electrodes for collecting the converted electric charges;
    irradiating radiation from a second imaging direction which is different from the first imaging direction;
    detecting the radiation irradiated from the second imaging direction by the radiation detector; and
    controlling at least one of the first and the second imaging directions to form a predetermined angle with respect to a direction that is orthogonal to a detector plane of the radiation detector;
    wherein a thickness d of the converting layer, a size p of the pixels and the predetermined angle θ satisfy the following formula (1):

$$d \cdot \tan \theta < k \cdot p \text{ ($k$ is a constant of 1 or less.)} \quad (1)$$

2. A radiation detector for detecting irradiated radiation comprising:
    a converting layer for converting radiation irradiated from a radiation source that is capable of irradiating radiation from two imaging directions, which are different from each other, into electric charges; and
    a plurality of pixel electrodes for collecting the converted electric charges detects the irradiated radiation, wherein in the case that one of two imaging directions forms a predetermined angle with respect to a direction that is orthogonal to a detector plane of the radiation detector, the thickness d of the converting layer, the size p of the pixels and the predetermined angle θ satisfy the following formula (1):

$$d \cdot \tan \theta < k \cdot p \text{ ($k$ is a constant of 1 or less.)} \quad (1)$$

3. The radiation detector as claimed in claim 2, wherein the k is a constant of 0.5 or less.

4. A radiographic imaging apparatus comprising:
    a radiation source capable of irradiating radiation from two imaging directions, which are different from each other; and
    the radiation detector as claimed in claim 3.

5. The radiographic imaging apparatus as claimed in claim 4 further comprising:
    a mechanism which can be selectively equipped with a plurality of the radiation detectors each having a different thickness d of the converting layer and/or a different size p of the pixels;
    an imaging angle setting means for receiving a setting of the predetermined angle θ; and
    an adapted detector specification means for specifying a radiation detector that satisfies formula (1) at the set predetermined angle θ.

6. The radiographic imaging apparatus as claimed in claim 5 further comprising:
    a mechanism which can be selectively equipped with a plurality of the radiation detectors each having a different thickness d of the converting layer and/or a different size p of the pixels;
    a detector specification means for specifying the radiation detector which has been loaded therein; and
    an adapted imaging angle determination means for determining the predetermined angle θ that satisfies formula (1) in the specified radiation detector.

7. The radiographic imaging apparatus as claimed in claim 4 further comprising:
    a mechanism which can be selectively equipped with a plurality of the radiation detectors each having a different thickness d of the converting layer and/or a different size p of the pixels;
    a detector specification means for specifying the radiation detector which has been loaded therein; and
    an adapted imaging angle determination means for determining the predetermined angle θ that satisfies formula (1) in the specified radiation detector.

8. A radiographic imaging apparatus comprising:
    a radiation source capable of irradiating radiation from two imaging directions, which are different from each other; and
    the radiation detector as claimed in claim 2.

9. The radiographic imaging apparatus as claimed in claim 8 further comprising:
    a mechanism which can be selectively equipped with a plurality of the radiation detectors each having a different thickness d of the converting layer and/or a different size p of the pixels;
    an imaging angle setting means for receiving a setting of the predetermined angle θ; and
    an adapted detector specification means for specifying the radiation detector that satisfies formula (1) at the set predetermined angle θ.

10. The radiographic imaging apparatus as claimed in claim 9 further comprising:
    a mechanism which can be selectively equipped with a plurality of the radiation detectors each having a different thickness d of the converting layer and/or a different size p of the pixels;

a detector specification means for specifying a radiation detector which has been loaded therein; and an adapted imaging angle determination means for determining the predetermined angle θ that satisfies formula (1) in the specified radiation detector.

11. The radiographic imaging apparatus as claimed in claim 8 further comprising:

a mechanism which can be selectively equipped with a plurality of the radiation detectors each having a different thickness d of the converting layer and/or a different size p of the pixels;

a detector specification means for specifying a radiation detector which has been loaded therein; and an adapted imaging angle determination means for determining the predetermined angle θ that satisfies formula (1) in the specified radiation detector.

* * * * *